(12) United States Patent
Gatto

(10) Patent No.: US 7,759,883 B2
(45) Date of Patent: Jul. 20, 2010

(54) DUAL-ROTARY-COUPLING, INTERNAL-WAVEGUIDE LINAC FOR IORT

(76) Inventor: Pompilio Gatto, Via Fontanile Anagnino No. 161, Rome (IT) 00118

( * ) Notice: Subject to any disclaimer, the term of this patent is extended or adjusted under 35 U.S.C. 154(b) by 441 days.

(21) Appl. No.: 11/877,699

(22) Filed: Oct. 24, 2007

(65) Prior Publication Data

US 2008/0129229 A1 Jun. 5, 2008

(30) Foreign Application Priority Data

Oct. 24, 2006 (EP) .................................. 06425734

(51) Int. Cl.
*H05H 9/00* (2006.01)
*H01J 35/10* (2006.01)
(52) U.S. Cl. ...................... 315/505; 315/506; 315/501; 315/500; 378/144; 378/147; 378/65; 378/68
(58) Field of Classification Search ................. 315/505, 315/506, 501, 500; 378/65, 68, 64, 144, 378/147, 145, 143

See application file for complete search history.

(56) References Cited

U.S. PATENT DOCUMENTS 7,619,374 B2 * 11/2009 Aoi et al. ..................... 315/500
2008/0043910 A1 * 2/2008 Thomas ........................ 378/65

* cited by examiner

*Primary Examiner*—Tuyet Vo
(74) *Attorney, Agent, or Firm*—Young & Thompson

(57) ABSTRACT

Electromedical apparatus for intraoperative radiotherapy via a linac. It includes an arm in which, at an extremity thereof, an oscillator is assembled which generates electromagnetic waves, and which supports, at an opposite extremity thereof, a radiating head in which a linac is assembled, emitting at its output an electron beam, supplied by the oscillator through a guiding structure. The apparatus includes a first and a second rotary couplings, respectively including a fixed portion and a mobile portion, endowed with sensors of the angular position of the mobile portions, which support the radiating head on the arm in roll and pitch motion. The guiding structure includes three separate rigid waveguides, of which one at the output of the oscillator and one of input to the linac, and an intermediate one therebetween, which connects them, with the heads of which they are respectively connected through the first and the second rotary couplings.

3 Claims, 1 Drawing Sheet

DUAL-ROTARY-COUPLING, INTERNAL-WAVEGUIDE LINAC FOR IORT

DISCLOSURE OF THE INVENTION

1. Technical Field

Figure 1:
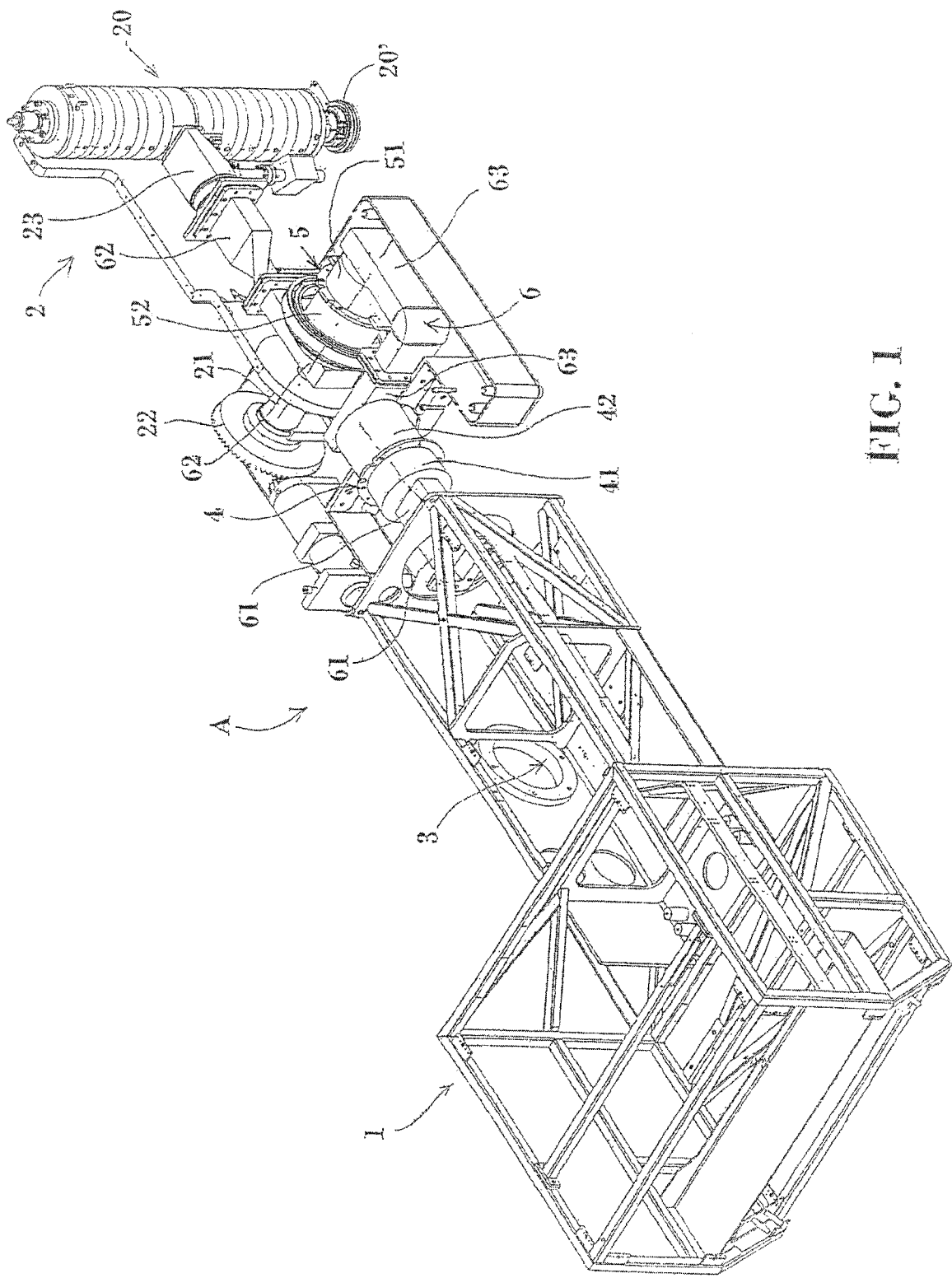

The present invention relates to a mobile electromedical apparatus for Intraoperative RadioTherapy (or "IORT") by means of an electron Linear Accelerator (or "linac").

2. Background Art

An electron linac is an evacuated waveguide in which a high-frequency traveling electromagnetic wave is excited, the axial electric field of which accelerates electrons. The phase velocity of the wave is made equal to the velocity of electrons by assembling irises in the guide, which delimitate accelerating coupled resonant cavities. The linac is supplied by a radiofrequency (or "RF") oscillator, particularly a cavity magnetron, through a guiding structure or means (any structure or means being meant, by such an expression, fit for guiding electromagnetic waves, e.g. rectangular or circular waveguides, and coaxial cables). A feature of a linac is the collimation of the beam, i.e. the parallelism of the trajectories of the electrons it emits.

A mobile "linac for IORT" is a mobile apparatus for applying radiations to produce a destructive effect on a tumour tissue. Electron irradiation has the advantage relative to photon irradiation of penetrating in the tumour tissue in a modulated manner (according to the desired depth), with the exclusion of surrounding healthy tissues. The surgeon after the removal of a tumour fixes the area to be treated with the radiotherapist and selects the energy of the beam with the sanitary physicist to administer the proper dose at a set depth.

A known-art apparatus includes a mobile radiating head, or shortly "head", containing an irradiation group including a linac. The beam emitted by this one is collimated by means of an applicator and scattered through the interaction with air existing inside the applicator. The applicator includes an upper applicator, directly connected with the radiating head, and a lower applicator, which is arranged in the surgical breach. With the object in view of the treatment, the upper applicator, in an operating stage of docking (i.e. of aligning and coupling) is brought in axis with the lower applicator, at a short distance from it, and connected to it through a ring nut.

The radiating head is supported by a "stand", including an articulated arm assembled on a motor mobile bedplate by a coupling which allows its yaw and pitch. The radiating head is assembled to the arm by a coupling which allows its roll and pitch.

In known-art apparatuses the irradiation assembly is assembled in the radiating head, and the RF generator assembly is assembled in the arm of the stand, separately from the radiating head, beyond the coupling of this one. The waveguide that connects the linac to the RF generator assembly is a flexible waveguide that steps over the coupling of the radiating head, passing outside the apparatus, and which in operation bends and twists, correspondingly assuming bending and twisting configurations.

Problems are connected with such an external flexible waveguide, which are overcome by the mobile radiotherapy linac forming the subject-matter of unpublished European Patent Application EP06425479, having the title "Internal-Waveguide Mobile Linac for Radiation Therapy", filed on 10 Jul. 2006, in the name of the same Applicant of the present application. Document EP06425479 relates to an electromedical apparatus for intraoperative radiation therapy by means of an electron linear accelerator, including an arm including means for generating electromagnetic waves, which arm supports a radiating head including means for linear acceleration of electrons, connected with the means for generating electromagnetic waves through guiding means, and for such an apparatus it teaches a fabricating solution according to which the guiding means include two waveguide tracts reciprocally connected through a rotary coupling, a waveguide tract of which, that passes between the head and the arm, being a flexible waveguide. In this way the external waveguide is substituted with an internal waveguide.

DISCLOSURE OF THE INVENTION

With the solution taught in Document EP06425479, however, there is still a flexible waveguide present, which restrictions are connected to. Indeed, it is subject to a wear rate, and it determines a limit to the freedom of pitch angular range of the radiating head within ±45°.

Moreover, the present invention takes its steps from ascertaining that the knowledge is important of the angular position of the head in space (with respect to a reference)—which also depends on the product of its pitch and roll rotations (with respect to the same reference)—in the progress of its operation, with the object of the docking manoeuvre and for a correct positioning of a radioprotection element, said the "beam absorber", under the operating bed. The beam absorber, typically composed of a lead cubic block having a thickness of 15 cm, it is necessary to absorb the "hard" energy-loss radiation, or Brehmsstrahlung, emitted by the electrons of the beam, at the output of the linac, passing through the body of the patient. Indeed, this radiation is dangerous for the persons who are in or pass through the places below the operating room. The beam absorber is to be centred on the electron beam at the output of the linac, the position whereof is also determined by the roll and pitch rotations. On the contrary, the deformations the flexible guide undergoes in its operation do not allow a precise measurement of the pitch angular position of the radiating head.

Moreover the aforesaid knowledge is useful to remotely verify the good working status of the apparatus, which can be tested by checking the right response of it to commands.

Therefore, it is the object of this invention to provide an internal-waveguide linac for IORT wherein the aforesaid flexible waveguide and the restrictions connected thereto are removed; particularly, wherein the radiating head has a pitch angular range of ±90°; and wherein the pitch angle of the radiating head turns out to be precisely measured, so that the angular position thereof, as results also from the roll and pitch rotations thereof, and, consequently, the direction in space of the electron beam at the output of the linac assembled in the head turn out to be precisely computable.

Such an object is reached according to this invention by providing that a linac apparatus for IORT includes, in combination, a first rotary coupling and a second rotary coupling, which support the radiating head of the apparatus on the arm of the stand respectively movable in roll and pitch; and that the guiding means for supplying the linac include three mechanically separate tracts, whereof an extreme tract of output from the means for generating electromagnetic waves and an extreme tract of input to the electron linear acceleration means, and an intermediate tract therebetween, that connects them, with the heads whereof the extreme tracts are respectively put in electric continuity through the first and the second coupling. Thus all the guiding means, no more subjected to any deformation in the progress of the rotations of the radiating head, can be rigid waveguides, and the object of the present invention is reached.

The second rotary coupling when rotating can provide the measure of the pitch angle of the radiating head.

The present invention envisages that means are provided for sensing the respective, pitch and roll, angular positions of the movable portions of the two rotary couplings, e.g. an encoder in correspondence with each one. The sensed values provided by such means can thus be provided to computing means, in functional communication therewith, fit for computing, based on such roll and pitch, the angular position of the electron beam and all the data connected therewith for the docking maneuvers and the positioning of the beam absorber. The computing means can provide these values to display means for an operator or to an automatic control system of the apparatus.

Therefore, it is the subject-matter of this invention an electromedical apparatus for intraoperative radiation therapy by means of an electron linear accelerator according to annexed independent Claim 1. Preferred embodiments are set forth in dependent Claims.

BRIEF DESCRIPTION OF FIGURES IN THE DRAWINGS

The present invention will be fully understood based on the following detailed disclosure of a preferred embodiment thereof, only given as a matter of example, absolutely not of restriction, referring to the annexed drawing, wherein:

FIG. 1 represents a perspective view of a linac for IORT according to the present invention.

BEST MODE FOR CARRYING OUT THE INVENTION

Articulated arm A is represented in FIG. 1 of a linac apparatus for IORT, comprising at a first extremity thereof a housing 1 intended to contain a high-voltage power-supply and a RF generator assembly including an oscillator, e.g. a cavity magnetron or a klystron. At a second extremity, opposite the first one, arm A supports a radiating head 2 including an electron linac 20, endowed with an output diaphragm 20' of the electron beam emitted by the linac.

Arm A is assembled through an arm coupling 3 which supports it in pitch motion, on a link (not represented) built for being assembled in yaw motion on a motor mobile bedplate (not represented). The coupling of arm 3 finds itself in an intermediate position between housing 1 and radiating head 2.

Radiating head 2 is mechanically assembled onto articulated arm A by means of the combination of a first and of a second rotary coupling. First rotary coupling, or roll coupling 4 includes a fixed portion 41, integral with arm A, and a mobile portion 42. Second rotary coupling, or pitch coupling 5, preceptive, includes a fixed portion 51 integral with mobile portion 42 of roll coupling 4, and a mobile portion 52 assembled integral with linac 20. The rotation axis of pitch coupling 5 can be perpendicular to the rotation axis of roll coupling 4.

Radiating head 2 is supported by a pivoting 63 having its rotation axis coaxial with the one of second coupling 5 and engaged by a gearwheel 22 through which the pitch motion thereof is actuated.

The electromagnetic waves at the output of the RF oscillator are transferred to linac 20 through a waveguide assembly 6, including three mechanically separate tracts, of which an extreme one 61 at the output of the oscillator and an extreme one 62 at the input of the linac (through an insertion rigid waveguide stub 23), connected through an intermediate tract 63, with the heads whereof they are respectively put in electric continuity through first and second rotary couplings 4 and 5.

The aforementioned combination of dual rotary coupling and three-tract waveguide assembly, apparently will allow the rotations in both rolling and pitching of the head, without deformation of the waveguide tracts. So, all these ones can be formed of rigid waveguides.

It is envisaged that encoders, or other means (not illustrated) are provided for sensing the respective, pitch and roll, angular positions of the mobile portions of the two rotary couplings, in correspondence with each one of them, in conjunction with a circuit board or other computing means, in functional connection with the encoders, fit for computing the position of the electron beam at the output of the linac, also based on such pitch and roll positions. Means for sensing the angular positions and circuit boards fit for the aforementioned object fall within the skill of the average man of the art and therefore will not be described herein.

The present invention has been described and illustrated referring to a preferred embodiment thereof, but it is to be expressly understood that variations, additions or omissions can be made thereto, without departing from the relevant scope of protection, which only remains restricted by the annexed claims.

The invention claimed is:

1. Electromedical apparatus for intraoperative radiotherapy by means of an electron linear accelerator, including an arm (A) including means for generating electromagnetic waves, wherein said arm supports a radiating head (2), wherein said radiating head includes means for the linear acceleration of electrons (20), emitting an electron beam at an output (20') of said means that generates electromagnetic waves through guiding means (6), characterized in that the guiding means includes in combination a first rotary coupling (4) and a second rotary coupling (5), respectively, wherein each rotary coupling includes a fixed portion (41, 51) and a mobile portion (42, 52), wherein the portions support said radiating head (2) upon said arm (A) respectively in pitch and in roll motion; said guiding means (6) including three mechanically separate tracts, of which an extreme tract (61) at the output of said means for generating electromagnetic waves and an extreme tract (62) of input (23) to said electron linear acceleration means (20), and an intermediate tract (63) therebetween to connect the extreme tracts and the three tracts (61, 62, 63) connect with the radiating head (2), wherein said extreme tracts (61, 62) are respectively put into electric continuity through said first and second rotary couplings (4, 5).

2. Apparatus according to claim 1, wherein said tracts (61, 62, 63), included by said guiding means (6), are rigid waveguides.

3. Apparatus according to claim 1, further including means for sensing angular positions of said mobile portions of said rotary couplings.

* * * * *